(12) United States Patent
Kralick (10) Patent No.: US 11,690,739 B1
(45) Date of Patent: Jul. 4, 2023

(54) IMPLANTABLE DEVICE FOR TREATMENT OF HYDROCEPHALUS

(71) Applicant: Francis A. Kralick, Wellington, FL (US)

(72) Inventor: Francis A. Kralick, Wellington, FL (US)

(*) Notice: Subject to any disclaimer, the term of this patent is extended or adjusted under 35 U.S.C. 154(b) by 0 days.

(21) Appl. No.: 17/002,154

(22) Filed: Aug. 25, 2020

(51) Int. Cl.
*A61F 2/848* (2013.01)
*A61F 2/82* (2013.01)
*A61F 2/86* (2013.01)

(52) U.S. Cl.
CPC ............ *A61F 2/848* (2013.01); *A61F 2/86* (2013.01); *A61F 2002/823* (2013.01); *A61F 2002/8483* (2013.01); *A61F 2250/0013* (2013.01)

(58) Field of Classification Search
None
See application file for complete search history.

(56) References Cited

U.S. PATENT DOCUMENTS

| | | |
|---|---|---|
| 4,432,853 A | 2/1984 | Banks |
| 4,474,569 A | 10/1984 | Newkirk |
| 5,897,528 A | 4/1999 | Schultz |
| 6,027,863 A | 2/2000 | Donadio, III |
| 6,030,358 A | 2/2000 | Odland |
| 6,107,004 A | 8/2000 | Donadio, III |
| 6,405,079 B1 | 6/2002 | Ansarinia |
| 6,503,231 B1 | 1/2003 | Prausnitz et al. |
| 6,537,232 B1 | 3/2003 | Kucharczyk et al. |
| 6,589,198 B1 | 7/2003 | Soltanpour et al. |
| 6,913,589 B2 | 7/2005 | Dextradeur et al. |
| 7,037,288 B2 | 5/2006 | Rosenberg et al. |

(Continued)

FOREIGN PATENT DOCUMENTS

| | | |
|---|---|---|
| EP | 0066685 | 12/1982 |
| WO | WO00/74763 | 12/2000 |

(Continued)

OTHER PUBLICATIONS

Emam et al., "A Novel Microdevice for the Treatment of Hydrocephalus: Design and Fabrication of an Array of Microvalves and Microneedles", Microsystem Technologies, 14, 371-378 (2008).

(Continued)

*Primary Examiner* — Leslie Lopez
(74) *Attorney, Agent, or Firm* — Caesar Rivise, PC (57) ABSTRACT

An implantable device for the treatment of hydrocephalus using a stent having a peripheral wall and an interior passageway and wherein a plurality of microneedles project outwardly from the peripheral and each needle includes a microneedle passageway from an aperture adjacent a distal end of the microneedle to a proximal end of the microneedle adjacent the peripheral wall. A corresponding plurality of one-way microvalves is positioned at the proximal ends of the microneedle and wherein the microneedle passageway is in fluid communication with the interior passageway whenever the one-way microvalve is open. When the stent is implanted in the superior sagittal sinus with the distal end of the plurality of microneedles positioned within the subarachnoid space and at least one of the plurality of microvalves is open, the stent permits cerebrospinal fluid to pass from the subarachnoid space to the superior sagittal sinus.

11 Claims, 7 Drawing Sheets

(56) References Cited

U.S. PATENT DOCUMENTS

| | | | |
|---|---|---|---|
| 7,118,548 | B2 | 10/2006 | Borgensen |
| 7,691,077 | B2 | 4/2010 | Kralick et al. |
| 8,206,334 | B2 | 6/2012 | Kralick et al. |
| 8,672,871 | B2 | 3/2014 | Heilman et al. |
| 9,199,067 | B2 | 12/2015 | Heilman et al. |
| 9,387,311 | B1 | 7/2016 | Heilman et al. |
| 9,545,505 | B2 | 1/2017 | Heilman et al. |
| 9,662,479 | B2 | 5/2017 | Heilman et al. |
| 9,669,195 | B2 | 6/2017 | Heilman et al. |
| 9,724,501 | B2 | 8/2017 | Heilman et al. |
| 9,737,696 | B2 | 8/2017 | Heilman et al. |
| 9,737,697 | B2 | 8/2017 | Heilman et al. |
| 10,058,686 | B2 | 8/2018 | Heilman et al. |
| 10,112,036 | B2 | 10/2018 | Heilman et al. |
| 10,272,230 | B2 | 4/2019 | Malek et al. |
| 10,279,154 | B2 | 5/2019 | Heilman et al. |
| 10,307,576 | B2 | 6/2019 | Heilman et al. |
| 10,307,577 | B2 | 6/2019 | Malek et al. |
| 10,596,357 | B2 | 3/2020 | Heilman et al. |
| 10,625,060 | B2 | 4/2020 | Borgensen |
| 10,625,061 | B2 | 4/2020 | Borgensen |
| 10,758,718 | B2 | 9/2020 | Malek et al. |
| 10,765,846 | B2 | 9/2020 | Heilman et al. |
| 2004/0106904 | A1 | 6/2004 | Gonnelli et al. |
| 2005/0043673 | A1 | 2/2005 | Lieberman |
| 2005/0096580 | A1 | 5/2005 | Moskowitz et al. |
| 2005/0159697 | A1 | 7/2005 | Dextradeur et al. |
| 2010/0256549 | A1* | 10/2010 | Kralick ............... A61M 27/006 604/9 |

FOREIGN PATENT DOCUMENTS

| | | |
|---|---|---|
| WO | WO01/66065 | 9/2001 |
| WO | WO2007/130718 | 11/2007 |

OTHER PUBLICATIONS

Wang et al., "A Parylene Micro Check Valve", IEEE 1999 International Micro Electro Mechanical Systems, 1999.
Choi et al., "Three Dimensional MEMS Microfluidic Perfusion System for Thick Brain Slice Cultures", Biomed Microdevices (2007) 9:7-13.
Dalvi, A., "Normal Pressure Hydrocephalus", WebMD, Inc., © 2021, retrieved on May 24, 2021 from: https://www.emedicinehealth.com/normal_pressure_hydrocephalus/article_em.htm.
Abstract of Chen et al., "A Multichannel Neural Probe for Selective Chemical Delivery at the Cellular Level", IEEE Transactions on Biomedical Engineering, 44(8), 760-769, 2001.
Abstract of Choi et al., "An Electrically Active Microneedle Array for Electroporation of Skin for Gene Delivery", The 13th International Conference on Solid-State Sensors, Actuators and Microsystems, Digest of Technical Papers, vol. 2, Transducers '05, (2005).
"A worldwide leader in cardiology and endovascular devices. Cardinal Health and Cordis", Cardinal Health, © 2021, retrieved on May 24, 2021 from https://www.cordis.com/global-home html.
Abstract of Czosnyka et al., "Laboratory Evaluation of the Phoenix CRx Diamond Valve", Neurosurgery 48(3), 689-93, 2001.
Abstract of Davis et al., "Hollow Metal Microneedles for Insulin Delivery to Diabetic Rats", IEEE Transactions on Biomedical Engineering, 52(5), 909-915,2005.
Abstract of Drake et al., "Randomized Trial of Cerebrospinal Fluid Shunt Valve Design in Pediatric Hydrocephalus", Neurosurgery, vol. 43, Issue 2, pp. 294-303, 1998.
Drake et al., "The Shunt Book", Blackwell Scientific, New York, 1995, Preface.
Abstract of Gardeniers et al., "Silicon Micromachined Hollow Needles for Transdermal Liquid Transport", Journal of Microelectromechanical Systems, vol. 12, Issue 6, pp., 855-862, 2003.
Abstract of Geschke et al., "Microsystem Engineering of Lab-on-a-Chip Devices", Wiley-VCHVerlag GmbH & Co. KGaA, © 2004.
Abstract of Hashmi et al., "Genetic Transformation of Nematodes Using Arrays of Micromechanical Piercing Structures", BioTechniques, 19(5), 766-770, 1995.
Heilman et al., "Anatomical Characterization of the Inferior Petrosal Sinus and Adjacent Cerebellopontine Angle Cistern for Development of an Endovascular Transferal Cerebrospinal Fluid Shunt", Journal of NeuroInterventional Surgery, vol. 11, Issue 6, 2019.
Henry et al., "Microfabricated Microneedles: A Novel Approach to Transdermal Drug Delivery", Journal of Pharmaceutical Science, vol. 87, No. 8, pp. 922-925, 1998.
Kralick, F. A., "Neurosurgical Treatment of Hypothalamic Hamartoma Producing Intractable Gelastic Seizures and Precocious Puberty", Journal of the American Organization of Neurological Surgeons and ACOS Neurological Section, vol. 1, pp. 17-22, 2001.
Abstract of Kralick et al., "Micro-Fabricated Shunt to Mimic Arachnoid Granulations for the Treatment of Communicating Hydrocephalus", Acta Neurochirurgica Supplement, 2012;114:239-42.
Lin et al., "Silicon-Processed Microneedles", Journal of Microelectromechanical Systems, vol. 8, No. 1, pp. 78-84, 1999.
Abstract of Liu et al., "Household Magnets Can Change the Programmable Shunt Valve in Hydrocephalus Patients", Proceedings of the IEEE 31st Annual Northeast Bioengineering Conference, 2005.
Abstract of Ilzhofer et al., "Development of Passive Microvalves by the Finite Element Method", Journal of Microelectromechanics and Microengineering, vol. 5, No. 3, pp. 226-230, 1995.
Abstract of Man et al., "Microfabricated Capillary-Driven Stop Valve and Sample Injector", IEEE, Eleventh Annual International Workshop on Micro Electro Mechanical Systems, pp. 45-50,1998.
McAllister et al., "Microfabricated Microneedles for Gene and Drug Delivery", Annual Review of Biomedical Engineering, vol. 2, pp. 289-313, 2000.
"Hydrocephalus", Medline Plus, retrieved on Sep. 15, 2021 from https://medlineplus.gov/ency/article/001571.htm.
"Hydrocephalus Fact Sheet", National Institute of Neurological Disorders and Stroke, retrieved on Jun. 3, 2020 from https://www.ninds.nih.gov/Disorders/Patient-Caregiver-Education/Fact-Sheets/Hydrocephalus-Fact-Sheet#44093125.
Abstract of Noh et al., "Parylene Gas Chromatographic Column for Rapid Thermal Cycling", Journal of Microelectro Mechanical Systems, vol. 11, Issue 6, pp. 718-725, 2002.
Noh et al., "Miniature Corrugated Diaphragm for Fiber-Optic-Linked Pressure Sensing (FOLPS)", Proceedings of IMECE '03, 2003 ASME International Mechanical Engineering Congress, 2003.
Abstract of Noh et al., "Parylene Micromolding, a Rapid and Low-Cost Fabrication Method of Parylene MicroChannel", Sensors and Actuators B: Chemical, vol. 102, Issue 1, pp. 102, 78-85, 2004.
Abstract of Noh et al., "Wafer Bonding Using Microwave Heating of Parylene Intermediate Layers", Journal of Micromechanics and Microengineering, vol. 14, pp. 625-631, 2004.
Abstract of Patwardhan et al., "Implanted Ventricular Shunts in the United States: The Billion-dollar-a-year Cost of Hydrocephalus Treatment", Neurosurgery, vol. 56, Issue 1, pp. 139-145, 2005.
Prausnitz, M., "Microneedles for Transdermal Drug Delivery", Advanced Drug Delivery Reviews, No. 56, pp. 581-587, 2004.
Abstract of Rajamaran et al., "Rapid, Low Cost Microfabrication Technologies Toward Realization of Devices for Dielectrophoretic Manipulation of Particles and Nanowires", Sensors and Actuators B: Chemical, vol. 114, Issue 1, pp. 392-401, 2006.
Abstract of Reed et al., "Micromachined Devices for Intravascular Drug Delivery", Journal of Pharmaceutical Science, 87(11), pp. 1387-1393, 1998.
Abstract of Shoji, S., Fluids for Sensor Systems, Topics in Current Chemistry, 194, pp. 163-188 (1998).
Simeone et al., "Posterior Instrumentation of the Cervical Spine Using the Concepts Unison System", Spinal Instrumentation: Surgical Techniques, Thieme Medical Publishers, pp. 336-338, 20005.
Stechison et al., The Trigeminal Evoked Potential: Part 1, Long-Latency Responses in Awake or Anesthetized Subjects, Neurosurgery, 33(4), pp. 633-638, 1993.
Abstract of Trautmann et al., "Replication of Microneedle Arrays Using Vacuum Casting and Hot Embossing", The 13th International (56) References Cited

OTHER PUBLICATIONS

Conference on Solid-State Sensors, Actuators and Microsystems, 2005, Digest of Technical Papers, Transducers '05, (2005).

Wang et al., "A Normally Closed-in-Channel Micro Check Valve", Proceedings IEEE Thirteenth Annual International Conference on Micro Electro Mechanical Systems, 2000.

Yoon et al., "Micro Devices for a Cerebrospinal Fluid (CSF) Shunt System", Sensors and Actuators A, 110(1), pp. 68-76, 2004.

Xie et al., "Surface Micromachined Leakage Proof Parylene Check Valve", 14th IEEE International Conference on Micro Electro Mechanical Systems, 2001.

Junqueira et al., "Basic Histology", 10th edition, The McGraw Hill Companies, 2003. Preface.

Madou, M., "Fundamentals of Microfabrication", 2nd Edition, CRC Press, 2002, pp. 580-585.

\* cited by examiner

IMPLANTABLE DEVICE FOR TREATMENT OF HYDROCEPHALUS

BACKGROUND OF THE INVENTION

The present invention relates generally to a shunting device for treatment of hydrocephalus, and more specifically to an implantable device for the treatment of hydrocephalus.

In order to better understand the prior art for treating hydrocephalus as well as the unique implantable device of the present invention, the following brief discussion of the mechanism responsible for hydrocephalus should be helpful; although not necessary for a person skilled in the art.

Cerebrospinal fluid (CSF) is a water-like fluid produced in the brain that circulates around and protects the brain and spinal cord, as is well known to those skilled in the art. It is believed that CSF is absorbed into the superior sagittal sinus, a venous structure that drains blood from the brain, through biologic one-way valves referred to as arachnoid villi or granulations, which pierce the dura mater. The arachnoid granulations are exposed to cerebral spinal fluid that resides in the subarachnoid space on the basal side and with the venous blood of the superior sagittal sinus on the apical side. Hydrocephalus is an abnormal accumulation of CSF within the subarachnoid space of the brain due to impaired CSF absorption. As is known, the subarachnoid area is the region around the brain and is bounded by dura mater. The dura mater comprises the walls of the superior sagittal sinus.

Hydrocephalus (HCP) is the abnormal accumulation of cerebral spinal fluid normally produced in the brain, most commonly as the result of impaired absorption with abnormal increase in intracranial pressure. The arachnoid granulations are the site of cerebral spinal fluid (CSF) absorption. They act as the interface between CSF and venous blood. HCP occurs in all age groups, can be acquired or congenital and associated with severe disability and death within hours if left untreated due to increased intracranial pressure. This data shows pediatric hydrocephalus accounts for 38,200-39,000 hospital admissions averaging 391,000 to 433,000 admission days and cost in the United States is estimated from 1.4 to 2.0 billion dollars annually. In adults, HCP occurs after trauma or aneurysm rupture. Military personnel develop HCP 14% of the time after traumatic brain injury. In the elderly, normal pressure hydrocephalus produces dementia HCP is one of the most frequently encountered problems in neurosurgery. One of the most common methods of treating hydrocephalus is through a surgical procedure in which a tube, referred to as a "shunt," is placed into the patient's body. The shunt system for diverting CSF from the intracranial compartment was developed in the 1950's, and has remained virtually unchanged for the past 50 years.

Essentially, the prior art shunts are implanted in a human body to channel the flow of CSF away from the brain into another part of the body. These prior art shunt devices generally include a single tube provided by a proximal catheter within the ventricular space and a distal draining catheter located within an absorptive surface of the body. Between the proximal and distal ends catheters is an intervening one-way valve device that is placed subcutaneously outside of the skull to limit the flow of CSF in one direction, i.e., away from the brain and direct the flow into the absorptive surface through the distal draining catheter. The most common absorptive surface employed in the prior art is the peritoneum of the abdominal cavity. It consists of a tube passing through the skull into the brain, tunneled under the skin to the abdomen where it is inserted into the peritoneal space; there is an inline valve that can be many different types. This type of shunt system is referred to as a ventriculo-peritoneal (VP) shunt. Although VP shunts have operated successfully to prevent death and disability resulting from hydrocephalus, they do have a number of shortcomings.

The first major shortcoming of the current VP shunt is its high failure rate. Failure rates are exceedingly high at 40% at 2 years and 90% at 5 years. Moreover, it is estimated that 50% of mechanical shunt failure is due to shunt blockage, which is usually highest in the immediate post-operative period. Specifically, the proximal catheter can become occluded if the brain debris or parts of choroid plexus become attached to the pores of the proximal catheter resulting in diminished flow. The valve between the proximal and distal catheters also may become occluded by debris, blood clot or infection. Bacterial infections in the blood can seed the long course of the shunt tubing from the head to the abdomen resulting in failure. Other causes of failure include tubing breakage, kinking or shortening due to patient growth or movement. All of the above-mentioned factors result in the published failure rate set forth above. As can be envisioned, this high failure rate results in frequent patient visits to the Emergency Room, frequent diagnostic procedures, hospitalizations and repeat surgery for shunt revisions. In addition to the high failure rate of prior art shunts posing a potentially dangerous situation for the patient, the high failure rate also results in increased health care costs. While the economic costs are believed to be enormous, the human cost of multiple hospital visits and surgical procedures, especially in the pediatric population simply cannot be measured. It is not improved by differing valve designs and anti-siphon devices. Programmable valves can be changed by magnets and require interrogation and reprogramming. Improper drainage may in part be due to the large pressure differential between the brain and the abdomen especially with change in posture and activity. High failure rates may be due to a critical design flaw of the single lumen tube. Its long course is prone to breakage and disconnection. Erosion through the skin and abdominal viscera is common. Scarring occurring within the abdomen leads to failed absorption. Infection rates leading to failure after initial placement are 5-9% requiring re-operation. VP shunts require repeated surgical procedures for revision and lengthening. Despite large prospective multicenter studies recent systematic literature review reported little high-quality data to guide best treatment practice. A paradigm shift is necessary in order to improve the vast economic cost and still larger human cost.

An additional problem encountered with current VP shunts is the imprecise flow of CSF, e.g., over- or under-shunting. Under-shunting occurs when CSF is not evacuated from the brain fast enough to maintain equilibrium with its production within the brain. In this situation, the VP shunt has not adequately treated the hydrocephalus. The limitations of valve design as well as some partial occlusion can produce this under-shunting. Over-shunting is also a limitation of the current shunt design, in which too much flow is allowed through the valve to thereby create an undesired lower than normal pressure around the brain. Such a low pressure usually is exacerbated by changes in a patient's posture from a recumbent to an erect position. In addition, a siphon effect can additionally lead to problems of over-drainage.

In an attempt to solve problems of imprecise shunting programmable valves (electromagnetically adjustable) have been commercialized. One supplier of such valves is Cordis.

These programmable valves permit neurosurgeons to preselect one of multiple pressure settings of the valve at the time of implantation. After implantation, the valve can be adjusted non-invasively using a magnetic device to individualize the flow rate to a particular patient's situation. This means that surgeons are able to make adjustments to help control intracranial pressure as a function of CSF elimination. However, the actual intracranial pressure cannot be monitored after implantation, and a change in pressure setting will be variable based on whether the patient is erect or recumbent. Also, it has been reported in the literature that household magnets can change the programmable shunt valves, thereby resulting in a failure of the shunting system. Thus, the use of electromagnetically adjustable, programmable shunting valves has not proven to be a great advantage, and still being prone to other problems, such as shunt failure, breakage, clogging, and infection. Moreover, these valves do not adapt to changing patient positions once having been set.

Anti-siphon devices also have been employed to correct problems of over shunting due to changes in patient position. As reported in the medical literature, this also has not alleviated the problems associated with imprecise flow.

Around 2004, an active shunt system was proposed, which consisted of a micro telemetry pressure sensor, a micro pump, and a controller. In this system, the controller controls the micro pump according to the intracranial pressure created by the CSF and measured with the telemetry pressure sensor. It is Applicant's understanding that pressure sensor and micro pump prototypes have been tested in-vitro. Although this particular approach could possibly provide an active form of moving CSF in relation to instantly measured pressure gradients, and also might be useful in monitoring the intracranial pressure after implantation for diagnostic purposes, there are still many obstacles to overcome with this later proposed system, e.g., power supply, complex circuitry, multiple moving parts, as well as the earlier mentioned problems of the current systems; namely, breakage, clogging, infection and the use of only a single outlet.

The following patents disclose prior art systems for the treatment of hydrocephalus (HCF): U.S. Pat. No. 4,432,853 (Banks); U.S. Pat. No. 5,897,528 (Schultz); U.S. Pat. No. 6,027,863 (Donadio, III); U.S. Pat. No. 6,030,358 (Odland); U.S. Pat. No. 6,107,004 (Donadio, III); U.S. Pat. No. 6,589,198 (Soltanpour, et al.); U.S. Pat. No. 6,913,589 (Dextradeur); U.S. Pat. No. 7,037,288 (Rosenberg, et al.); and U.S. Pat. No. 7,118,548 (Borgesen).

Moreover, U.S. Pat. No. 7,691,077 (Kralick, et al.) and U.S. Pat. No. 8,206,334 (Kralick, et al.) disclose implantable micro-systems for treating HCF. Although the systems disclosed therein overcome many of the problems of the prior art, they too suffer from the need to utilize highly invasive surgery, requiring the surgeon to implant them at the subarachnoid space side of the dura mater.

The present invention is believed to have the capability of overcoming virtually all of the problems associated with the prior art shunting systems, as described above and while avoiding the need to implant the invention at the subarachnoid space side.

All references cited herein are incorporated herein by reference in their entireties.

BRIEF SUMMARY OF THE INVENTION

An implantable device for the treatment of hydrocephalus in a living being by permitting the passage of cerebrospinal fluid (CSF) from the subarachnoid space to the superior sagittal sinus of the skull is disclosed. The device comprises a stent including a peripheral wall and an interior passageway provided by the peripheral wall. And wherein the stent comprises a plurality of microneedles that project outwardly from the peripheral wall, wherein each one of the microneedles includes a needle passageway from an aperture adjacent a distal end of the microneedle to a proximal end of the microneedle adjacent the peripheral wall; and a corresponding plurality of one-way microvalves, each one of which is positioned at the proximal end of a corresponding microneedle, and wherein the needle passageway is in fluid communication with the interior passageway whenever the one-way microvalve is open; and wherein the stent permits CSF to pass from the subarachnoid space to the sagittal sinus when stent is positioned in the superior sagittal sinus, the distal end of the plurality of microneedles is positioned within the subarachnoid space and at least one of the plurality of microvalves is open.

Preferably the fluid transmitting members are microconduits or micro-fibers that communicate with at least 50% of the microvalves; more preferably over 50% of the microvalves and most preferably with all of the microvalves.

In the preferred form of this invention, the microvalves permit the flow of CSF through the microneedles based on the pressure differential between the subarachnoid space at the distal end of the fluid transmitting members and the superior sagittal sinus at the proximal end of the microneedles. The microvalves of this invention are simplistic in design, having a minimum of moving parts without the need for a power source. The microvalves employed in this invention act as many micro-sized "flap valves" that open and close in response to the pressure differential between the subarachnoid space and the venous system of the sinus thereby mimicking the function of normal arachnoid granulations.

Most preferably, the plurality of microneedles is formed in a fixed array on a first substrate and the microvalves are formed in substantially the same fixed array on a second substrate. In accordance with this embodiment, the first and second substrates are secured together, e.g., by friction fitting the valves to corresponding needles and/or by thermal bonding contiguous surfaces of the first and second substrates together.

In the most preferred embodiment of this invention, the microneedles are substantially cone shaped, including a pointed distal end adapted to penetrate through the dura mater during the procedure of inserting the device in a patient's head.

Reference throughout this application to a "microneedle" means a needle having dimensions most commonly defined in micrometers, although the entire array of microneedles, as a unit, may have dimensions most commonly defined in units larger than micrometers, e.g., millimeters. Needles having dimensions outside the range of micrometers but that are capable of being maintained in an array for insertion into the skull of a human to treat hydrocephalus are considered to be within the scope of this invention. However, hollow microneedles are considered to be the most preferred needle structures for use in the device of this invention.

Reference to "microvalve(s)" in accordance with this invention, refers to valves designed to enclose a lower, or proximal end of the passage through each microneedle and being adapted to be in an opened condition to permit the flow of CSF through the needle, when desired to preclude an excessive build up of pressure within the subarachnoid area. The number, density and location of the devices of this invention may vary based on laboratory measurements, but a starting point will be an arrangement that produces a desired flow, which presently is believed to be on the order of roughly 4.52+/−0.43 microL/min per mm Hg/cm(2). That is, a plurality of individual units can be positioned in different locations within the skull and the size of the individual units can be varied to either increase or decrease the number and/or density of the microneedles in each unit.

Reference to "micro-conduits," micro-fibers," and the like mean conduits or fibers having dimensions most commonly defined in micrometers, although an entire array of microconduits and/or microfibers, as a unit, may have dimensions most commonly defined in units larger than micrometers, e.g., millimeters.

BRIEF DESCRIPTION OF SEVERAL VIEWS OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE PREFERRED EMBODIMENTS

Referring now to the figures, wherein like reference numerals represent like parts throughout the several views, exemplary embodiments of the present disclosure will be described in detail. Throughout this description, various components may be identified having specific values, these values are provided as exemplary embodiments and should not be limiting of various concepts of the present invention as many comparable sizes and/or values may be implemented.

Applicant has designed a microfluidic shunt device using MEMS technology that overcomes the basic design flaws of VP shunts. It is comprised of a 5×5 mm array of 100's of hollow microneedles, 500 microns in height each with a dome-shaped valve 250 microns in diameter. The microneedles transport CSF from the subarachnoid space to the venous blood by perforating the wall of the venous sinus that separates these two compartments. This strategy serves to mimic the location, multiplicity and pressure gradient seen by the arachnoid granulations. As described below, the present invention 20 includes microvalves that have been tested and that demonstrate proper flow rates of 0.3-0.5 ml/min with durability and without reflux. Multiple studies have shown the success of shunting CSF to the venous sinus (14-17). The pressure gradient between CSF and venous system keeps CSF in dynamic equilibrium with production. This eliminates over drainage due to siphoning effect or changes in the patient's posture. Failure rates can be dramatically reduced due to hundreds of outlets to prevent occlusion of a single lumen tube. This microdevice is simple in design with valves that function analogous to cardiac valves. This obviates the need for pumps, power, or electronics. It is not a "smart valve" but a "dumb valve". The small size as compared to a VP shunt eliminates breakage, perforation of viscera, erosion through skin, infection or repeated surgery for lengthening. Endovascular placement allows for a minimally invasive same day surgery without a craniotomy and can be produced at low cost.

CSF is produced in the brain (choroid plexus and ependymal lining of the ventricular space) at a rate of approximately 0.3-0.5 ml/minute. The average volume of intracranial CSF is 125 ml. The total volume of CSF is turned over 3-4 times in a 24 hour period [Pediatric Neurosurgery at the Univ. of Adelaide]. The production and absorption of CSF is therefore in a dynamic equilibrium. Although there is some controversy as to the exact mechanism by which CSF absorption takes place to thereby maintain a desired pressure level within the subarachnoid area, it is most widely held that the primary route for maintaining equilibrium is the result of CSF being permitted to move into the sinus through arachnoid granulations that pierce the dura mater of the sinus.

Specifically, the CSF pressure in the subarachnoid area varies according to age. In infants, it is estimated that the CSF pressure is between about 40 to 50 mmH$_2$O and in children, from 40-100 mmH$_2$O. In older age groups, the pressure remains constant at about 150 mmH$_2$O. Pressures above 200 mmH$_2$O are considered to be abnormal.

It also should be noted that the CSF pressure is usually about 40 to 50 mmH2O above the intracranial venous pressure. This difference in pressure is related to the continuous production of CSF and the resistance to its secretion.

Hydrocephalus is described as either non-communicating or communicating. The communicating form is a defect at the level of the arachnoid granulations/villi. The non-communicating type is caused by an obstruction to outflow within the interior of the brain. These pathological conditions of hydrocephalus can be life-threatening and result in brain injury if left untreated. They are caused by a number of different etiologies and effect both the pediatric and adult patient population.

Figure 1:
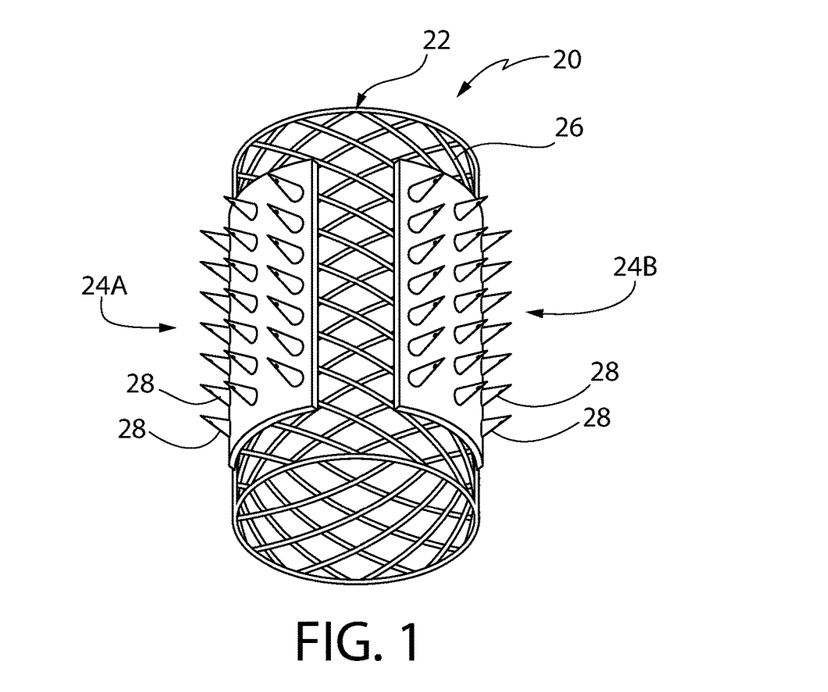
FIG. 1 is an isometric view of the implantable device for the treatment of hydrocephalus (HCP) showing two microneedle arrays on the outer peripheral wall of a stent portion.

The implantable device of the present invention is generally shown at 20 in FIG. 1 and comprises hollow cylindrical section 22, hereinafter referred to as a "stent" along with a pair of microneedle arrays 24A and 24B secured to a peripheral wall 26 of the stent 22. Each microneedle array 24A/24B comprises individual microneedles 28, shown by way of example only, as a cone-shaped configuration. Moreover, each microneedle array 24A comprises a plurality of microneedles 28 that, also by way of example only, are shown in three rows of seven microneedles 28. It should be understood that the number of microneedles and the arrangement of the microneedles in each array 24A/24B can vary and it is within the broadest scope of the present invention that all of these other configurations are covered by the present application.

Figure 2:
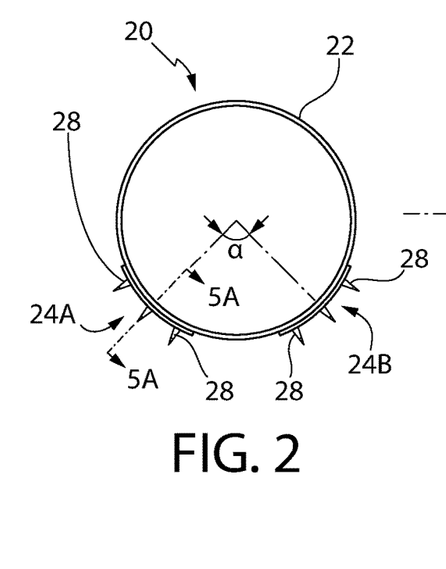
FIG. 2 is an end view of the implantable device of FIG. 1.
Figure 3:
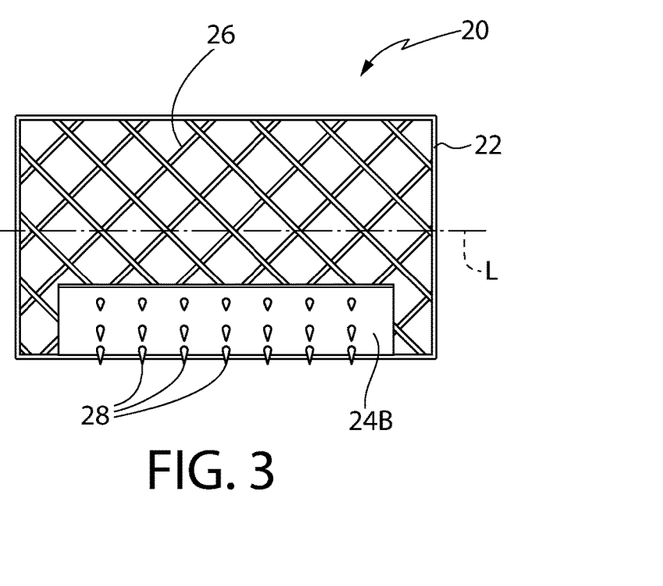
FIG. 3 is a side view of the implantable device of FIG. 1.
Figure 4A:
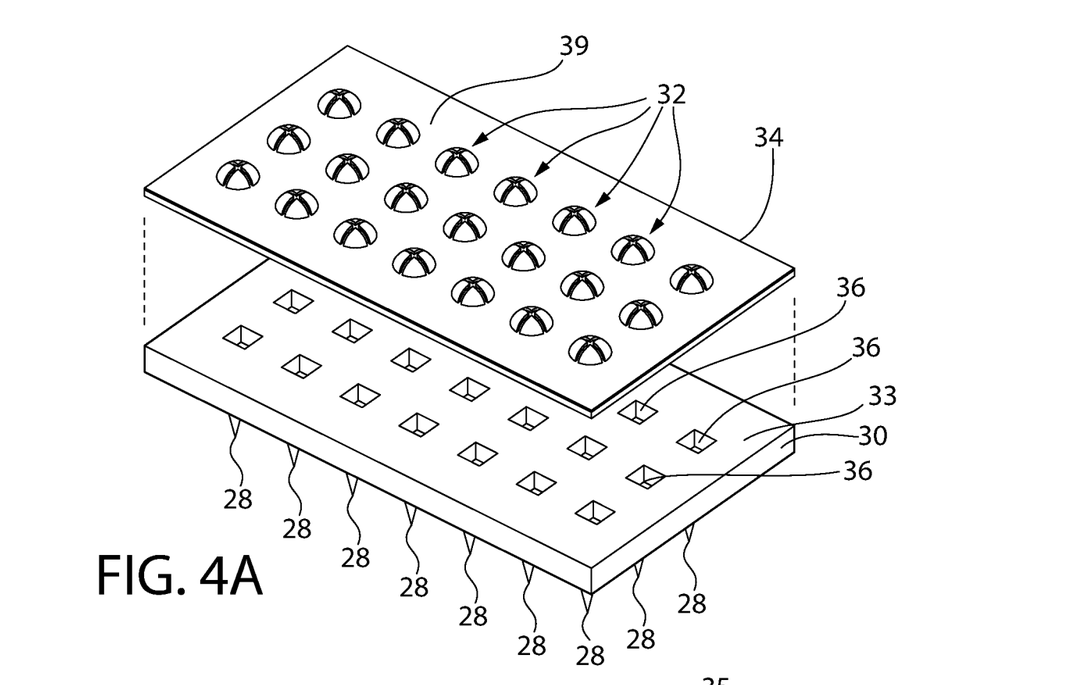
FIG. 4A is an exploded view of one of the microneedle arrays showing a first substrate of one-way microvalves aligned with corresponding proximal ends of the microneedles located on a second substrate.
Figure 4B:
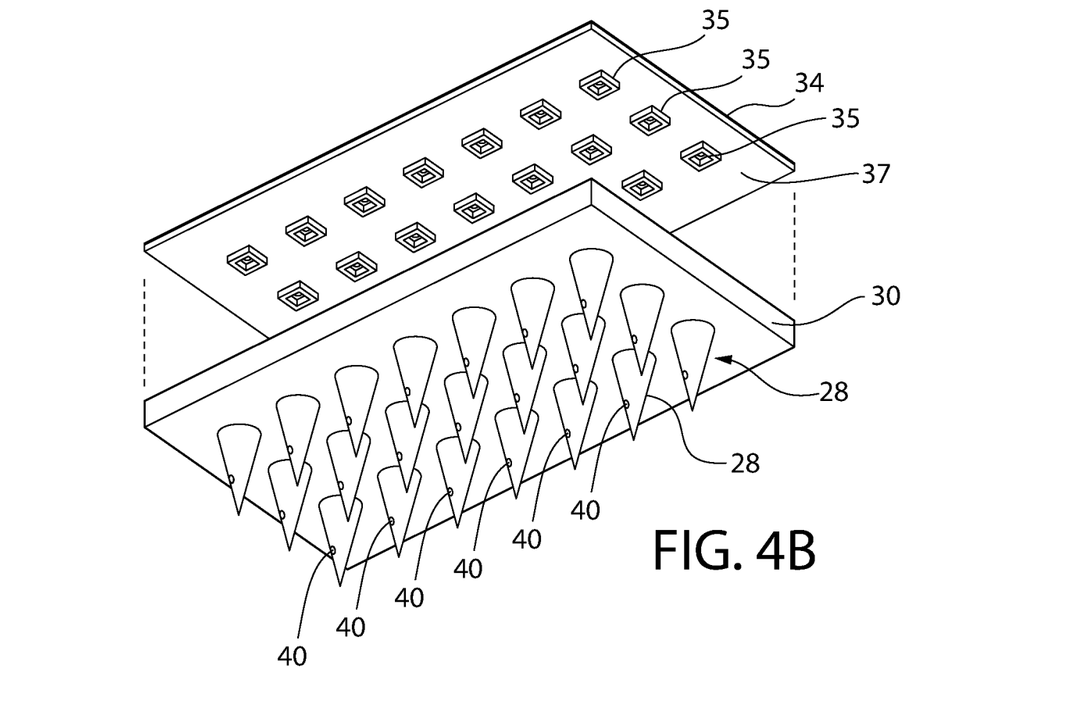
FIG. 4B is an exploded view of one of the microneedle arrays, similar to FIG. 4A, but taken from a bottom vantage point.

FIG. 2 is an end view of the implantable device 20 showing the orientation of the two microneedle arrays 24A/24B with respect to the peripheral wall 26 of the stent 22 and FIG. 3 provides a side view of the implantable device 20 having a longitudinal axis L. These figures depict the orientation of implantable device 20 when it is implanted within the superior sagittal sinus 8 (FIG. 6), with the distal ends (the pointed ends) of the microneedles piercing the dura mater 2 (FIG. 6) and positioned within the subarachnoid space 6 (FIG. 6), as will be discussed in detail later. By way of example only, the length of the stent 22 may be in the range of 1-3 cm, the diameter of the stent 22 may be in the range of 1-3 cm, and the angular separation a (FIG. 2) of the two microneedle arrays 24A and 24B may be approximately 90° where a is defined as angle having an apex at the center of the stent 22 and angle legs that pass through the center of the respective microneedle arrays 24A/24B FIGS. 4A-4B depict exploded views of one of the microneedle arrays 24A or 24B. As can be seen, each array 24A/24B comprises a plurality of microneedles 28 formed in a fixed array on a microneedle carrier substrate 30. The device 20 further includes a plurality of one-way microvalves 32 formed in a fixed array on a microvalve carrier substrate 34, with the microvalves 32 disposed in substantially the same array as the microneedles 28 formed in substrate 30 so that each of the microvalves 32 in the array cooperates with a corresponding hollow microneedle 28. By way of example only, the microneedle valve substrate 30 can be formed with openings 36 (see FIG. 4A) on a first side 33. Moreover, the microvalve substrate 34 can be formed with upstanding peripheral walls 35 surrounding each microvalve 32 on one side 37 of the microvalve substrate 34. As such, when the substrates 30 and 34 are joined together, the upstanding peripheral walls 35 fit snugly within the openings 36 as shown most clearly in FIG. 5B. This joined assembly 30/34 forms a flexible laminate and whereby the surface 39 (FIG. 4A) can be secured (e.g., thermal bonding, adhesively coupled, etc.) to the curved peripheral wall 26 of the stent 22, as shown most clearly in FIG. 1. Securing the surface 39 to the peripheral wall 26 of the stent 22 does not interfere in any manner with the microvalves' 32 operation since the microvalves 32 are located on the inside of the peripheral wall 26 (see, for example, FIG. 7).

Figure 8:
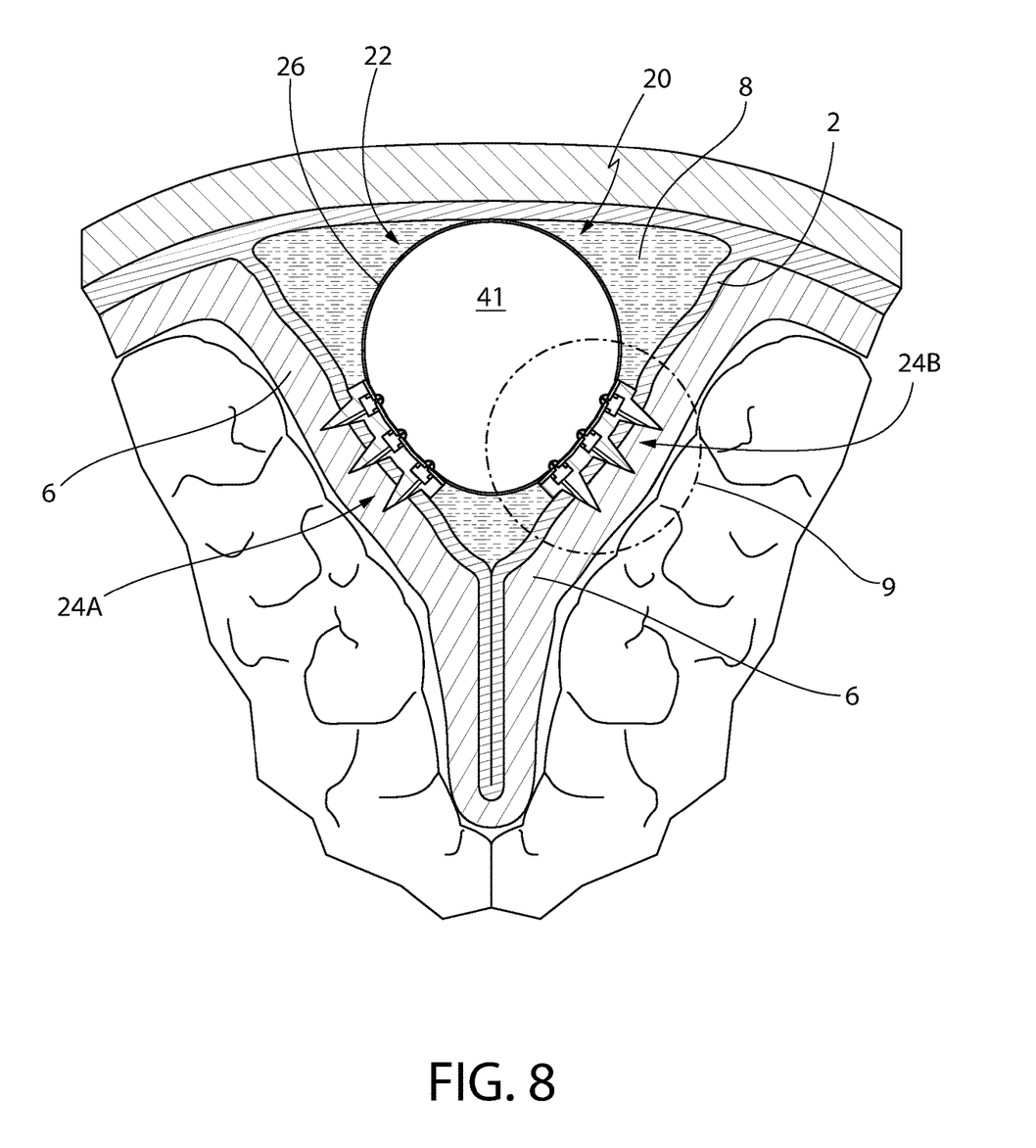
FIG. 8 is a cross-sectional view of the implantable device implanted in the superior sagittal sinus and taken along line 8-8 of FIG. 7.
Figure 9:
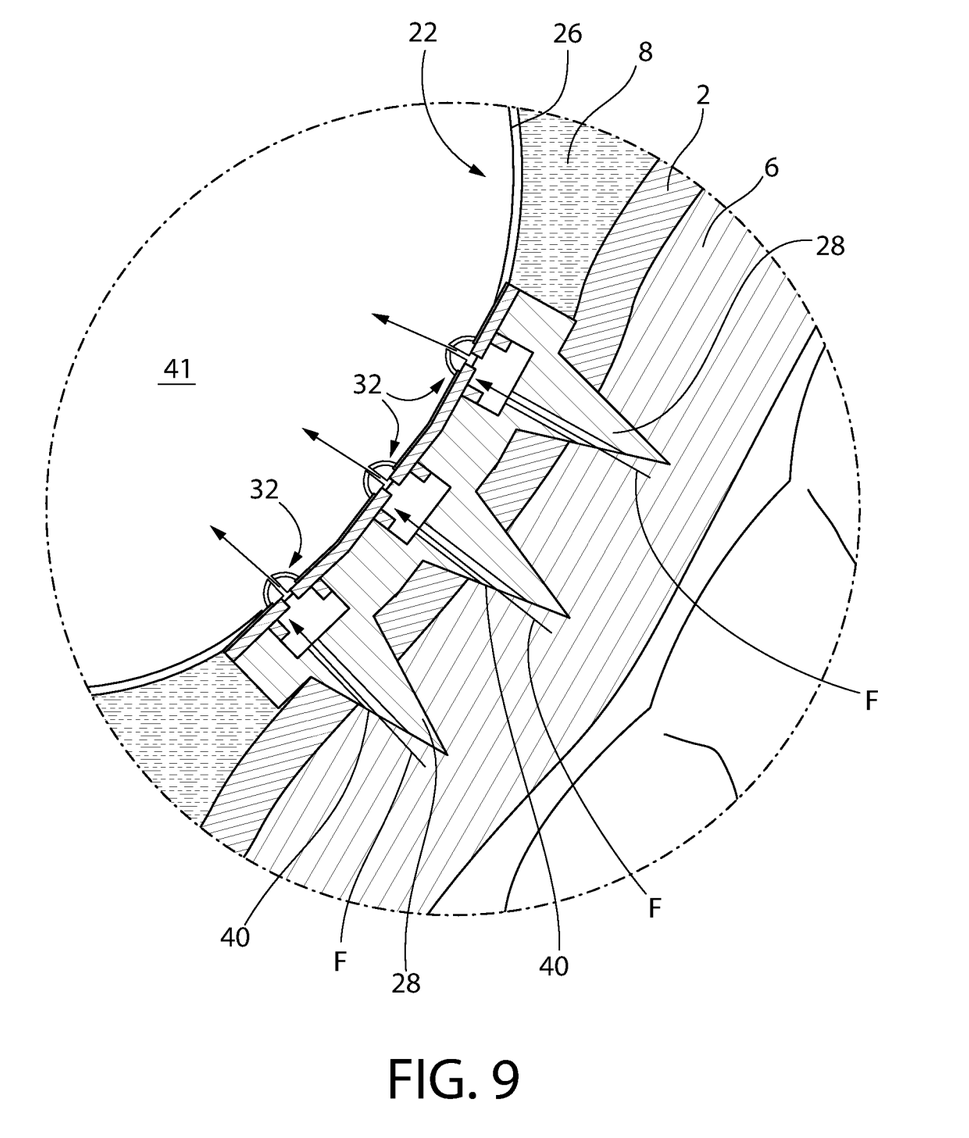
FIG. 9 is enlarged cross-sectional view of a portion (shown in FIG. 8) of the invention implanted in the superior sagittal sinus.

The device 20 of the present invention is surgically placed to pierce the dura mater 2 (FIGS. 6 and 8), and, in conjunction with their corresponding one-way valves 32, act as a one-way outlet for CSF. Specifically, microvalves 32 attached at the top, or proximal end of the microneedles 28 are intended to divert CSF to the venous system through the stent 22 at a given pressure. The outflow of CSF is controlled passively by the pressure differential between the venous channel and the subarachnoid space 6, in a manner very similar to a normally functioning arachnoid villi 4 biological system. Thus, the device 20 of this invention is intended to mimic the function of the normal CSF physiologic mechanism.

Figures 5A, 5B:
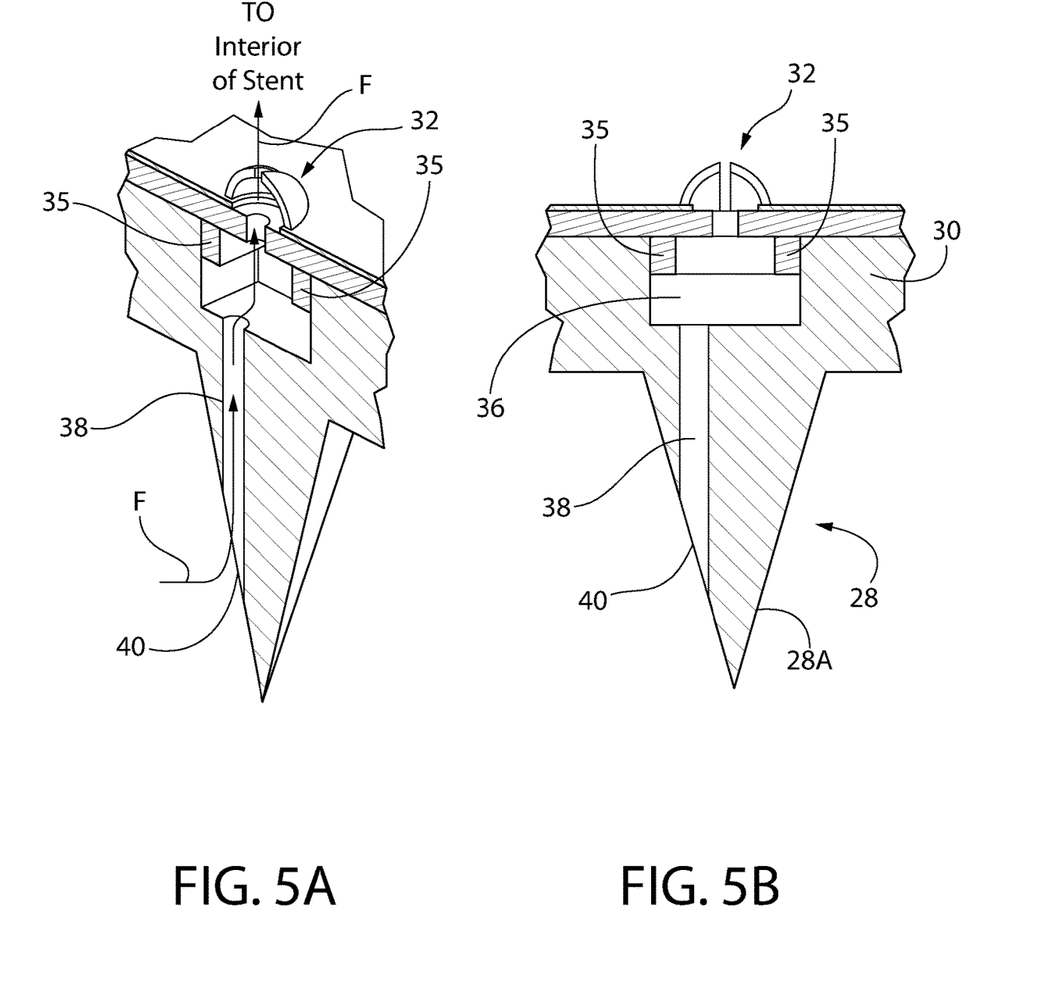
FIG. 5A is a cross-sectional view of one of the microneedles taken along line 5A-5A of FIG. 2 and depicting the flow of cerebrospinal fluid (CSF) through the microneedle, through the one-way microvalve, when opened, and into the stent portion (not shown)
FIG. 5B is a cross-sectional view of one of the microneedles.
Figure 6:
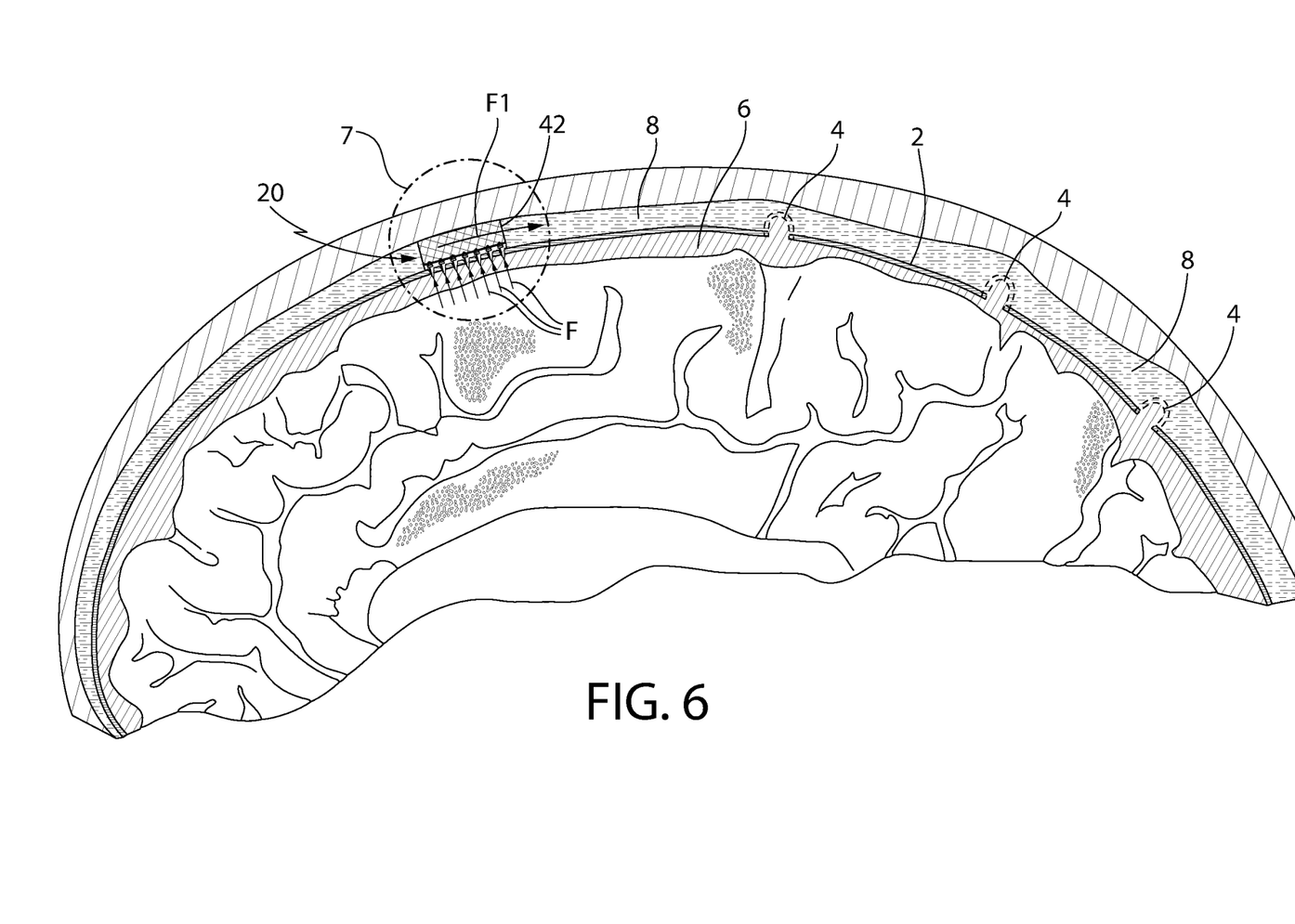
FIG. 6 is a partial cross-sectional view of the upper portion of a patient's skull/brain (also referred to as the "meninges region" of a human brain) showing the preferred location of implantation of the implantable device for the treatment of HCP.
Figure 7:
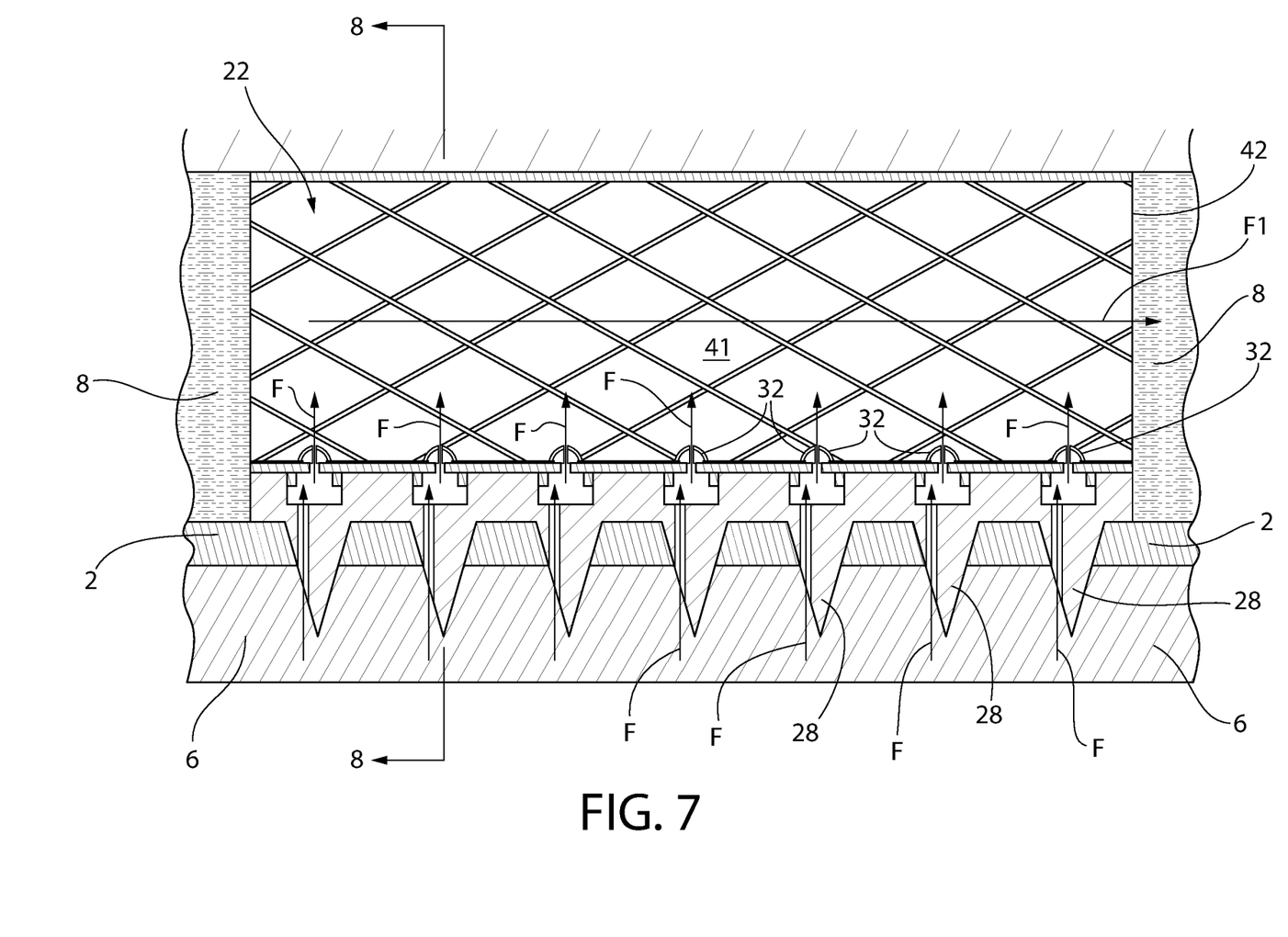
FIG. 7 is a cross-sectional view of the implantable device implanted in the superior sagittal sinus with the microneedle arrays piercing the dura mater and whose distal ends are positioned in the subarachnoid space while depicting the flow of CSF when the CSF pressure has exceeded the threshold pressure for opening the one-way microvalves.

As shown in FIGS. 5A-5B, in a preferred embodiment of this invention 20, each microneedle 28 is a generally cone-shaped, hollow member whose distal end 28A (FIG. 5B) is configured to pierce the dura mater 2 that forms the walls of the superior sagittal sinus 8 when the device 20 is implanted. In FIG. 5B, an enlarged opening 36 extends through the substrate 30 and communicates with a proximal end of a microneedle passageway 38 extending through microneedle 28. A distal end of the microneedle passageway 38 comprises an aperture 40 which is ultimately positioned within the subarachnoid space 6 when the device 20 is implant; and it is through this aperture 40 that CSF enters the microneedle passageway 38. The arrow F indicates the CSF flow from the subarachnoid space 6 into the superior sagittal sinus 8. As shown in FIG. 7, once the CSF flow F passes through the opened one-way microvalves 32, the CSF flow continues into the interior 41 of the stent 22 and the CSF flows toward the posterior end 42 of the stent 22, as indicated by the arrow F1. The flow F1 is the typical posterior flow direction, due to a pressure gradient in the superior sagittal sinus 8, of CSF that would normally pass through the arachnoid villi 4 from the subarachnoid space 6.

With the microneedle carrier substrate 30 and the microvalve carrier substrate 34 secured together, a corresponding one-way microvalve 32 is in fluid communication with the opening 36. Also, with the microneedle carrier substrate 30 and the microvalve carrier substrate 34 secured together and mounted to the peripheral wall 26 of the stent 22, each microvalve 32, in turn, is positioned within the interior of the stent 22. Thus, the microneedle passageway 38 through the microneedle 28 communicates with the subarachnoid space 6 of the brain, where CSF flows, and also with the superior sagittal sinus 8. The one-way microvalves 32 remain closed until the pressure difference between the subarachnoid space 6 and the superior sagittal sinus reaches a cracking pressure of the normally-closed microvalve 32, e.g., 10 mmH$_2$O, (the pressure required to "open", the normally-closed microvalve 32, also referred to as the "threshold pressure"). Once that cracking pressure is achieved, each one-way microvalve 32 will open, thereby permitting the flow of CSF up through the aperture 40, through the microneedle passageway 38, opening 36 and through the opened one-way microvalve 32 and into the interior of the stent 22. If desired, a detent-like surface or recess can be formed about the conical surface at the base thereof adjacent the substrate 30 to provide a region in which the tissue of the dura mater 2 can lock into place and thereby aid in holding the implantable device 20 in proper position.

It should be understood that the sinus 8 can be, but is not limited to, the superior sagittal sinus. The implantable device 20 is designed to simulate the generally normal performance of the arachnoid villi 4 (FIG. 6) in healthy patients. That is, the implantable device 20 is designed to function as a one-way valve device to maintain a desired pressure level (or prevent an excessively high pressure level) within the brain. Specifically, the implantable device 20 of this invention communicates the subarachnoid space 6 within the surrounding dura mater 2 with the sinus 8 (FIGS. 6-9).

It should be understood that the stent 22 is shown in the figures as a wire mesh configuration by way of example only. Alternatively, the stent 22 may comprise a solid peripheral wall with apertures provided therein to allow for passage of the plurality of microvalves 32 therethrough so that they reside in the interior of stent 22, as shown by example in FIG. 7. As such, the term "stent 22" is meant to convey a broad scope of biocompatible materials that act as a lumen to allow CSF that passes from the subarachnoid space 6 to the sagittal sinus space 8 through the microneedles 28 and microvalves 32 into the sagittal sinus space 8, while not interfering with normal fluid flow in the sagittal sinus space 8.

It is anticipated that the implantable device 20 of this invention can employ as many as 100 microneedles 28 and microvalves 32 in an array on respective, substantially square substrates 30/34 each of which is approximately 1 mm thick and has sides approximately 5 mm in length. Thus, in an embodiment wherein the microneedles 28 are disposed in a 10×10 array on a substrate having 5 mm sides, the microneedles 28 preferably have a maximum outside dimension of less than 0.5 mm. It also is envisioned that more than one device 20 can be implanted through the dura mater, depending on the flow of CSF required to maintain a desired pressure within the subarachnoid space 6.

As mentioned above, the microneedles 28 and the microvalves 32 are formed separately, and are included on respective substrates 30 and 34, which are joined together (e.g., by thermal bonding contiguous surfaces of the substrates together and/or by friction fitting the microvalves 32 within the enlarged openings 36 at the proximal end of respective microneedles 28.

The material forming the microvalves 32 must have low rigidity (that is, have low cracking pressure), as well as being biocompatible with the body. To meet these requirements, Parylen C (poly-monochloro paraxylylene) has been selected as the material for the device. Parylene C is a biocompatible, thin polymer film that is micromachinable. Moreover, it, as well as the other materials employed in the device 20 are compatible with current imaging modalities, such as CAT scan and MRI of the brain.

Although Parylene C has been identified as a preferred material for coating the microneedles 28 and manufacturing the microvalves 32, it should be understood that the specific materials employed are not considered to be a limitation on the broadest aspects of the present invention. People skilled in the art clearly will be able to select appropriate polymers and possibly other materials for use in fabricating the microneedles 28 and microvalves 32. In fact, useable materials are disclosed in an article entitled "Three dimensional MEMS microfluidic perfusion system for thick brain slice cultures," authored by Yoonsu Choi et al. and appearing in Biomed Microdevices (2007) 9:7-13. The subject matter of this latter article is hereby fully incorporated by reference herein.

It also should be understood that the specific construction of the microvalves 32 do not constitute a limitation on the broadest aspect of this invention. However, it should be noted that there are two types of valves with regard to their initial state; namely, the normally-opened valve and the normally-closed valve. The normally-opened valves stay open until the pressure reaches a certain point at which the membrane collapses and covers the orifice (i.e., closes the valve).

The normally-closed valves remain closed until the pressure difference reaches a cracking pressure at which the membrane is lifted, opening the valve to provide a fluid path. In order to avoid any back flow (from sinus 8 to the intracranial area 6), the normally closed valve is preferred for use in the present invention 20.

A number of preliminary valve designs were tested, with the two most desirable designs being selected on the basis of the ease of manufacturing and required valve parameters, e.g., cracking pressure and reverse flow prevention. The primary and most preferred design is the dome petal (DP) design, which is illustrated in the figures, and will be discussed in greater detail hereinafter, with regard to its method of manufacture. The second design is the four arm corrugated spring design (not shown), which is known in the art and does not need any further explanation herein.

The dome petal design is, as the name implies, a dome with a square base and the dome being cut in four equal segments, which normally are in a collapsed, or closed condition. The four arm corrugated spring design includes four arms fixed to four positions on the surface of a base and the four arms are attached to a square shaped plug stopper. The stopper is covering a flow hole, which is cut through the base. This arrangement acts like a flexible membrane that can open and close, altering the flow of the CSF from the subarachnoid space 6 into the sagittal sinus space 8. As noted above, Parylene C is preferred as the valve material for both designs.

In a representative embodiment, the base of each of the microvalves 32 was essentially square, having sides of approximately 300 micrometers in length and a depth or thickness of approximately 20 micrometers. An opening through the center of the base was approximately 50 micrometers in diameter. When constructed from Parylene C the base membranes had a negligible displacement of several nano-meters for a pressure difference of 100 Pa to 1000 Pa.

Both the dome petal and four arm corrugated spring designs were subjected to pressure-deflection analyses which revealed the following four points about the effects of various parameters, as follows: 1. As pressure increased across the valve, the displacement of the membrane increased. 2. As the membrane thickness increased, the displacement of the membrane decreased. 3. For the dome-petal construction, as the height of the dome increased the displacement of the membrane increased. 4. For the four arms corrugated spring construction, as the number of corrugation increases, the displacement in the membrane increased.

The four parameters associated with the performance of a check valve are cracking pressure, flow resistance in the forward direction, leakage in the reverse direction and maximum reverse blocking pressure. In order to investigate the four parameters, fluidic analysis is required to be coupled with structural analysis. People skilled in the art, clearly can investigate the operability of various different microvalves for the purpose of selecting an appropriate valve for use in the present invention.

The implantable device 20 permits the rate of CSF absorption to be tailored to the needs of the patient. By achieving this result, the invention 20 essentially restores the normal CSF equilibrium in the face of non-functioning native absorption sites while production remains constant.

The implantable device 20 allows the efflux of CSF from the subarachnoid space 6 as a result of the pressure differential between that area and the sinus 8 of the vascular outflow pathways of the brain, thus giving precise control of the intra-cranial pressure, closely mimicking the properly functioning arachnoid villi 4. The present device 20 needs to be capable of diverting the CSF at low pressure differences (<50 mmH$_2$O). Moreover, the device 20 desirably should open for the CSF to flow out but reliably close to prevent backflow. In addition, the device 20 needs to be designed to hold the CSF in the brain at a rate of change in pressure of 150-200 mmH$_2$O.

In order to mimic the functioning of the biological arachnoid villi 4, the implantable device 20 must be properly designed. Indeed, the size of the device 20 is a critical aspect of the invention. Specifically, the size is dictated by the fact that device 20 will be surgically implanted adjacent to the brain in the subarachnoid space 6, as illustrated in FIGS. 6-9. In particular, the device 20 will be implanted into the dura mater 2 in close proximity to the cerebral structures. Therefore, it is important that the device 20 be small and that it have a low profile. The passive device 20 of this invention obviates the need for multiple moving parts or for the use of any power supply. Employing active components that require a power supply and control units will make it very difficult to build a device that is sufficiently small to be placed within the confines of the skull, and also could have an adverse effect on the reliability of the device 20.

Moreover, the present invention 20 has redundancy built into the device; in view of the fact that the device 20 includes multiple microneedles 28 communicating the subarachnoid area 6 with the sinus 8. In particular, the dura mater 2 in a normally functional individual has many arachnoid granulations/villi 4 to drain CSF. The device 20 of this invention, employing multiple microneedles 28 has the same or similar redundancy. Thus, a redundant configuration of the type employed in the device 20 of this invention should lower the failure rate relative to prior art systems that rely on a single conduit.

Another important aspect of this invention 20 is the biocompatibility of the material with the body. Biocompatibility insures that the materials employed in the device 20 will be inert to the body and, therefore, that the body will not reject the device 20. In addition, blood clotting on the device 20 also needs to be avoided to reduce the failure rate.

Turning to the methods of this invention, one method of fabricating the array 24A/24B of microneedles 28 on the substrate 30 is disclosed in an article entitled "Three dimensional MEMS microfluidic perfusion system for thick brain slice cultures," authored by Yoonsu Choi et al. and appearing in Biomed Microdevices (2007) 9:7-13. The subject matter of this latter article already has been fully incorporated by reference herein. In addition, the manner of forming the array 24A/24B of microneedles 28 employed in the device 20 of this invention is disclosed in U.S. Pat. No. 7,691,077 (Kralick, et al.) and U.S. Pat. No. 8,206,334 (Kralick, et al.), both of which are incorporated by reference in their entireties.

Similarly, the manner of making the array of dome petal valves 32 employed in the preferred embodiment of this invention 20 will now be described. In addition, a Parylene check valve system useable in this invention also is disclosed in an article titled: "A Parylene Micro Check Valve," authored by Xuan-Oi Wang, et al., and appearing in the Proceedings of the IEEE Micro Electro Mechanical Systems (MEMS, 1999, pgs. 177-182 beginning on page 177 of the IEEE publication in 1999. Again, the manner of forming the array of microvalves 32 on the substrate 34 employed in the device 20 of this invention is disclosed in U.S. Pat. No. 7,691,077 (Kralick, et al.) and U.S. Pat. No. 8,206,334 (Kralick, et al.), both of which are incorporated by reference in their entireties. The only difference is that the upstanding walls, formed around the microvalves in U.S. Pat. No. 7,691,077 (Kralick, et al.) and U.S. Pat. No. 8,206,334 (Kralick, et al.), are rather formed beneath the microvalves 32 to form upstanding peripheral walls 35 in the present invention 20, as shown in FIGS. 4B and 5B.

Although the preferred embodiment discloses the formation of the microneedles 28 and microvalves 32 on distinct substrates that are then joined into a laminate secured to the peripheral wall 26 of the stent, it is within the broadest scope of the present invention 20 to have the microneedles 28 and microvalves formed integrally with the stent 22.

In summary, the implantable device 20 of this invention desirably mimics the number as well as the size of the native arachnoid villi 4, instead of employing a single outflow pathway to shunt CFS to a non-physiologic location as in the prior art shunting systems. Thus, the present invention 20 provides redundancy to avoid failure as a result of clogging of a single orifice. This array of multiple outlets provided through the microneedles 28 increases the reliability of the device 20 as compared to prior art systems having only a single pathway for the flow of CSF out of the subarachnoid space 6.

The device 20 is compact and has a high density of outflow pathways. It should be noted that maintaining the passages in close proximity could result in small obstructions potentially occluding many of the pathways. It is envisioned that this potential can be overcome by increasing the area of the device 20, while decreasing the density of the array of microneedles 28 and microvalves 32 associated with such microneedles 28. The thin profile of the device 20 will still fit against the sinus 8 in the subarachnoid space and would more closely mimic the physiologic system in which the native arachnoid villi 4 are located along the length of the sinus 8.

A concern of obstruction inherent in the device 20 of this invention is the possible obstruction of the tips of the microneedles 28 from clotting blood. This problem is believed to be correctable by the proper selection of size and orientation of the orifices of the microneedles 28 and also by the possible use of surface coatings on the microneedles 28 to prevent clotting. Shunt failure of prior art devices as the result of infection should also be drastically reduced with the device 20 of this invention, except possibly in cases of meningitis. Meningitis is an infection of the covering of the brain and results in the obstruction of normal arachnoid villi 4. Given the resemblance of the device 20 of this invention to the native arachnoid villi 4 this could be an uncommon source of obstruction in the present invention. However, other types of infection and therefore shunt failure commonly seen with prior art shunts should be eliminated by the design of the device 20.

Moreover, shunt failure as the result of tubing disconnection, cracking, kinking and shortening as a result of patient growth is similarly eliminated by the device 20 of this invention, since the present invention does not employ any long tube connecting the subarachnoid space 6 to the peritoneal cavity as in prior art constructions.

In addition, as mentioned previously, an improvement of the present invention 20 over the implantable micro-systems disclosed in U.S. Pat. No. 7,691,077 (Kralick, et al.) and U.S. Pat. No. 8,206,334 (Kralick, et al.) is that those micro-systems suffer from the need to utilize highly invasive surgery, requiring the surgeon to implant them at the subarachnoid space side of the dura mater. In contrast, the implantable device 20 of the present invention avoids the invasiveness into the subarachnoid space and rather permits the surgeon to implant from the skull level downward.

The implantable device 20 in accordance with this invention is compact and completely contained within the confines of the skull. The potential for damage is minimal as it is afforded the protection of the skull. The potential for dislodgement is minimized by proper placement and anchoring.

For safety considerations, the anterior one third of the sinus 8 would be the most logical site for implantation, as illustrated in FIGS. 6-9. In the event of tearing the wall of the sinus 8 during implantation, this section of vasculature can be sacrificed without producing neurological deficit.

From the above explanation it should be apparent that Applicant has invented a unique implantable device 20 that diverts CSF from the subarachnoid space 6 (FIG. 6) to the sinus 8 (FIG. 6), thereby mimicking normally functioning arachnoid granulations/villi 4 (FIG. 6) for the treatment of hydrocephalus. The implantable device 20 of this invention is intended to replace deficient arachnoid villi 4 and thereby produce the physiological condition of eliminating excess CSF pressure in the brain.

While the invention has been described in detail and with reference to specific examples thereof, it will be apparent to one skilled in the art that various changes and modifications can be made therein without departing from the spirit and scope thereof

What is claimed is:

1. An implantable device for treating hydrocephalus in a living being by permitting passage of cerebrospinal fluid (CSF) from a subarachnoid space to a superior sagittal sinus of a skull of the living being, said device comprising:
    a stent including a longitudinal axis, a peripheral wall and an interior passageway provided by said peripheral wall, said passageway defining open longitudinal ends of said stent, said stent comprising:
        a plurality of microneedles located in between said open longitudinal ends and that project outwardly from said peripheral wall, each one of said microneedles including a needle passageway from an aperture adjacent a distal end of said microneedle to a proximal end of said microneedle adjacent said peripheral wall; and
        a corresponding plurality of one-way microvalves, each one of which is positioned at said proximal end of a corresponding microneedle, said needle passageway being in fluid communication with said interior passageway whenever said one-way microvalve is open; and
    wherein said stent permits the CSF to pass from the subarachnoid space to the sagittal sinus when said stent is positioned in the superior sagittal sinus, said distal end of said plurality of microneedles are positioned within the subarachnoid space and at least one of said plurality of microvalves is open.

2. The implantable device of claim 1 wherein each one of said plurality of microvalves comprises segments moveable by a pressure build-up of CSF within said needle passageway to provide open communication between the subarachnoid space and the superior sagittal sinus.

3. The implantable device of claim 2 wherein said plurality of microneedles and said corresponding plurality of one-way valves are formed into two arrays, a first array being positioned at a first location on said peripheral wall and a second array being positioned at a second location, different from said first location, on said peripheral wall, said first array comprising a first group of microneedles and a corresponding first group of one-way microvalves and wherein said second array comprises a second group of microneedles and a corresponding second group of one-way microvalves.

4. The implantable device of claim 3 wherein said first array comprises a first substrate having said first group of microneedles thereon and a second substrate having said corresponding first group of one-way microvalves thereon, and wherein said second array comprises a third substrate having said second group of microneedles thereon and a fourth substrate having said corresponding second group of one-way microvalves thereon, said first and second substrates being contiguous to each other to thereby communicate each microvalve on said second substrate with the proximal end of a corresponding microneedle on said first substrate, and wherein said third and fourth substrates are contiguous to each other to thereby communicate each microvalve on said fourth substrate with the proximal end of a corresponding microneedle on said third substrate.

5. The implantable device of claim 4 wherein each one of said one-way microvalves in said second substrate includes an upstanding peripheral wall positioned within an opening in said first substrate that communicates with the proximal end of a corresponding microneedle in said first substrate, and wherein each one of said one-way microvalves in said fourth substrate includes an upstanding peripheral wall within an opening in said third substrate that communicates with the proximal end of a corresponding microneedle in said third substrate.

6. The implantable device of claim 4 wherein an outer surface of said upstanding peripheral wall of each microvalve in said second substrate frictionally engages internal surfaces of said opening in said first substrate, and wherein an outer surface of said upstanding peripheral wall in each microvalve in said fourth substrate frictionally engages internal surfaces of said opening in said third substrate.

7. The implantable device of claim 4 wherein said first and said second substrates are secured together and wherein said third and fourth substrates are secured together.

8. The implantable device of claim 1 wherein said corresponding plurality of microvalves permit a flow of the CSF through said plurality of microneedles based on a pressure differential between the subarachnoid space at said distal ends of said microneedles and the superior sagittal sinus at the proximal ends of said microneedles.

9. The implantable device of claim 1 wherein said plurality of microneedles are made of a polymer.

10. The implantable device of claim 1 wherein said plurality of microneedles are biocompatible within a human body.

11. The implantable device of claim 1 wherein at least some of said plurality of microneedles are generally cone-shaped and have a recess in an outer surface thereof for receiving dura mater therein to help retain said device in proper position when implanted.

* * * * *